United States Patent
Sapir

(10) Patent No.: US 9,742,314 B2
(45) Date of Patent: Aug. 22, 2017

(54) IMPLANTABLE MICRO POWER GENERATOR (IMPG)

(71) Applicant: Itzhak Sapir, Irvine, CA (US)

(72) Inventor: Itzhak Sapir, Irvine, CA (US)

(73) Assignee: Irvine Sensors Corp., Costa Mesa, CA (US)

( * ) Notice: Subject to any disclaimer, the term of this patent is extended or adjusted under 35 U.S.C. 154(b) by 0 days.

(21) Appl. No.: 14/940,461

(22) Filed: Nov. 13, 2015

(65) Prior Publication Data

US 2016/0156283 A1 Jun. 2, 2016

Related U.S. Application Data

(60) Provisional application No. 62/085,857, filed on Dec. 1, 2014.

(51) Int. Cl.
H01L 41/113 (2006.01)
H02N 2/18 (2006.01)
A61N 1/378 (2006.01)

(52) U.S. Cl.
CPC ............ *H02N 2/18* (2013.01); *A61N 1/3785* (2013.01); *H01L 41/1132* (2013.01); *H02N 2/181* (2013.01)

(58) Field of Classification Search
CPC .............. H01L 41/113; H01L 41/1132; H01L 41/1134; H01L 41/1136; H01L 41/1138
USPC .................................................. 310/338, 339
See application file for complete search history.

(56) References Cited

U.S. PATENT DOCUMENTS

2010/0298720 A1\* 11/2010 Potkay ................. A61B 5/0215
600/485

\* cited by examiner

*Primary Examiner* — Derek Rosenau

(57) ABSTRACT

An implantable device for harvesting in-vivo blood pressure fluctuations' energy to generate electrical power for powering medical implants while avoiding the need for external power sources.

11 Claims, 6 Drawing Sheets

Figure 3

IMPLANTABLE MICRO POWER GENERATOR (IMPG)

CROSS-REFERENCE TO RELATED APPLICATIONS

This application claims the benefit of U.S. Provisional Patent Application No. 62/085,857, filed on Dec. 1, 2014 entitled "Implantable Micro Power Generator (IMPG)" pursuant to 35 USC 119, which application is incorporated fully herein by reference.

STATEMENT REGARDING FEDERALLY SPONSORED RESEARCH AND DEVELOPMENT

N/A

BACKGROUND OF THE INVENTION

1. Field of the Invention

The invention relates generally to the field of Neuroprosthetics. More specifically, the invention relates to a device that will harvest power directly from a body process in the area of the sensor implant to allow operation of the implant without the need for batteries and without the risks and limitations associated with them.

2. Description of the Related Art

Current medical implants that require electrical power to operate use power from either an implanted battery pack or from an external wired power source. Another method for powering medical implants involves generating electrical power from chemical reactions of body fluids or tissues with an implanted power generator. No device is known to use blood pressure fluctuations for in-body power harvesting.

BRIEF SUMMARY OF THE INVENTION

Applicant discloses an Implantable Micro Power Generator (IMPG) as a device that harvests energy directly from an innate process of the body, blood pressure fluctuations, to power implanted brain and other sensors while eliminating the drawbacks of using batteries.

IMPG is a small, round and sealed device that is implanted in proximity to the brain and with direct fluidic coupling with an artery. The MPG is electrically wired to nearby medical implants to provide power for their operation.

These and various additional aspects, embodiments and advantages of the present invention will become immediately apparent to those of ordinary skill in the art upon review of the Detailed Description and any claims to follow.

While the claimed apparatus and method herein has or will be described for the sake of grammatical fluidity with functional explanations, it is to be understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112, are to be accorded full statutory equivalents under 35 USC 112.

BRIEF DESCRIPTION OF THE SEVERAL VIEWS OF THE DRAWINGS

The invention and its various embodiments can now be better understood by turning to the following FIGS. 1-7 and the description of the preferred embodiments which are presented as illustrated examples of the invention in any subsequent claims in any application claiming priority to this application. It is expressly understood that the invention as defined by such claims may be broader than the illustrated embodiments described below.

FIG. 3 is a data sheet of different off-the-shelf piezo disks that constitute the basis for the performance calculations presented in the detailed description of the invention.

DETAILED DESCRIPTION OF THE INVENTION

Turning now to the figures wherein like references define like elements among the several views, Applicant discloses an Implantable Micro Power Generator (IMPG) as a device that harvests energy directly from an innate process of the body. The IMPG will power implanted brain and other sensors while eliminating the drawbacks of using batteries.

IMPG is a small, round and sealed device that is implanted in proximity to the brain and with direct coupling with an artery in the head area such as the Common Carotid Artery. It is electrically wired to nearby sensors to provide power for their operation. The IMPG design is scalable to allow power generation levels as needed by the brain sensors. Although the description and image in FIG. 1 are for implantation in the head and for brain sensors, the IMPG can be implanted in any part of the body and be coupled with any artery.

The principle of operation of the Implantable Micro Power Generator is periodic spherical bending of a disk-shaped piezoelectric membrane resulting in generating a voltage differential across a power regulation and storage circuit. This voltage differential is harvested and stored in a capacitive storage means. The circuit then regulates the output power that is supplied to the end customers, the brain sensors.

Figure 2:
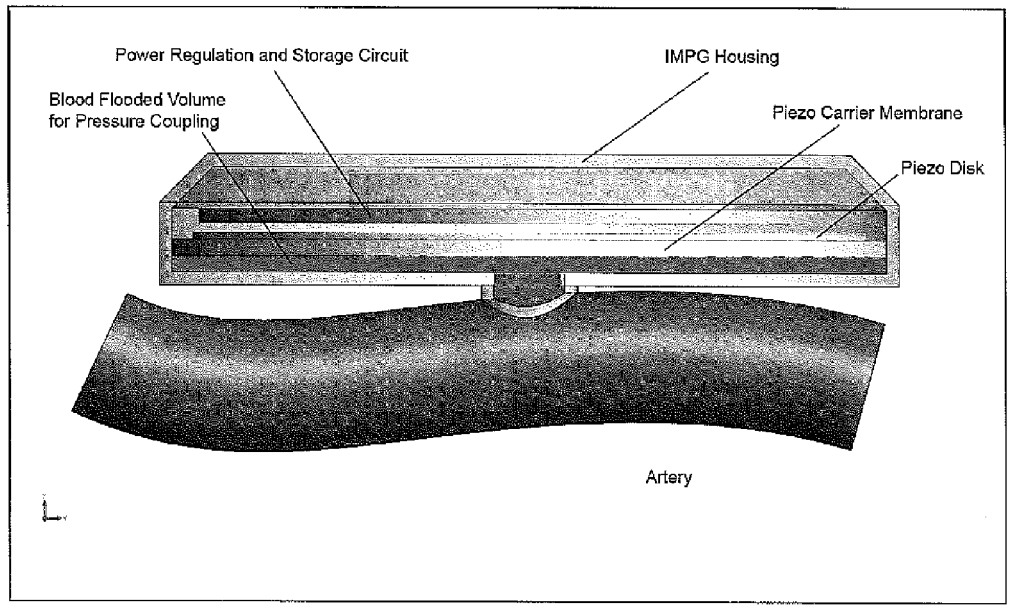
FIG. 2 depicts a cross section of the IMPG showing its main components and its direct coupling to a blood vessel in accordance with one preferred embodiment.

The IMPG consists of a small sealed chamber in a mechanical housing. One wall of the sealed chamber holds a piezo disk while on one of the other walls there is a port that makes direct coupling with a fluid, blood or intermediary fluid as will be described below. The fluid floods the chamber on one side of the piezo disk and pressure fluctuations create the spherical bending of the disk at twice the heart rate frequency, in-and-out from the relaxed (center) position. FIG. 2 shows a schematic presentation of the IMPG coupled with an artery and blood flooding one side of the piezo membrane.

Figure 1:
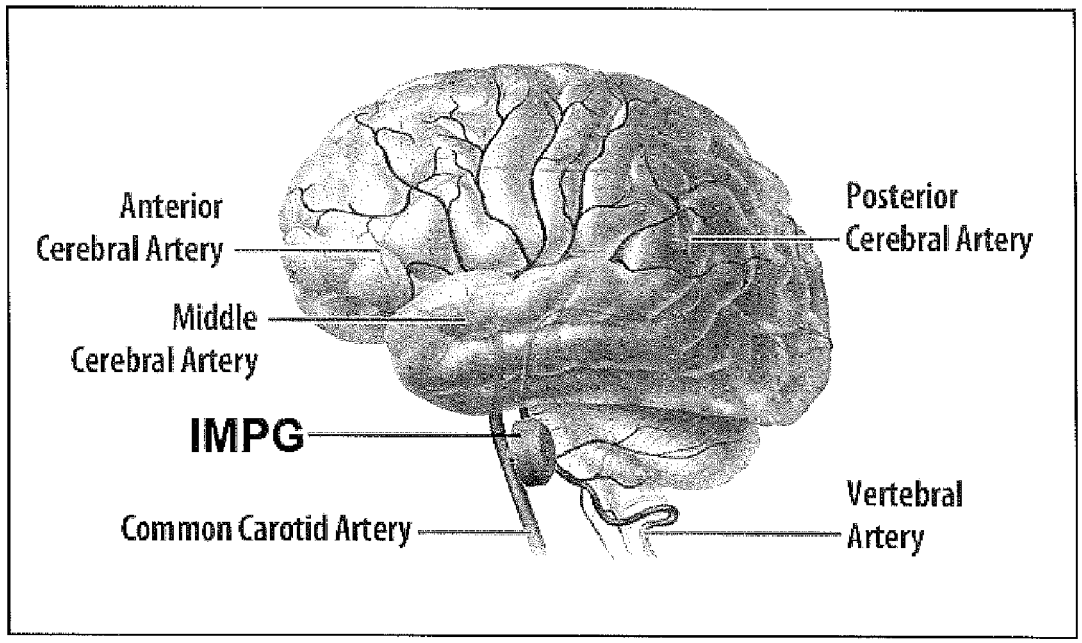
FIG. 1 depicts the IMPG implanted in the head area and directly coupled with a major brain artery.

The thickness of the IMPG based on components' thickness buildup in the preferred embodiment is 4 mm Although FIGS. 1 and 2 show the IMPG's coupling with the artery done in the area of implantation, the actual coupling can be done through an implanted tube to a blood vessel farther away. The main reason for doing this is reduced health risk by connecting to an artery that is not part of the brain blood supply while at the same time keeping the IMPG close to the electrical consumers, minimizing electrical losses for such small power levels. This also allows more flexibility in selecting the area for implantation for the IMPG.

One concern that may rise from the above description is the risk of blood clots in the stagnant blood volume trapped in the pressure coupling tube. These blood clots may block the pressure coupling tube and turn the IMPG inoperable. Even worse, blood clots can be released into the blood stream and cause a stroke. In one embodiment of the invention, a second membrane will separate the fluid inside the pressure coupling tube, referred to as intermediary fluid, from the blood stream at the area of connection between the tube and the artery. Blood that flows over the membrane will never be stagnant thus will not create clots. The intermediary fluid inside the pressure coupling tube and the IMPG will not be blood and will therefore not introduce the risk of blocking the tube. The membrane at the end of the tube is very thin and flexible in order to minimize the amount energy lost to its bending.

Figure 3:
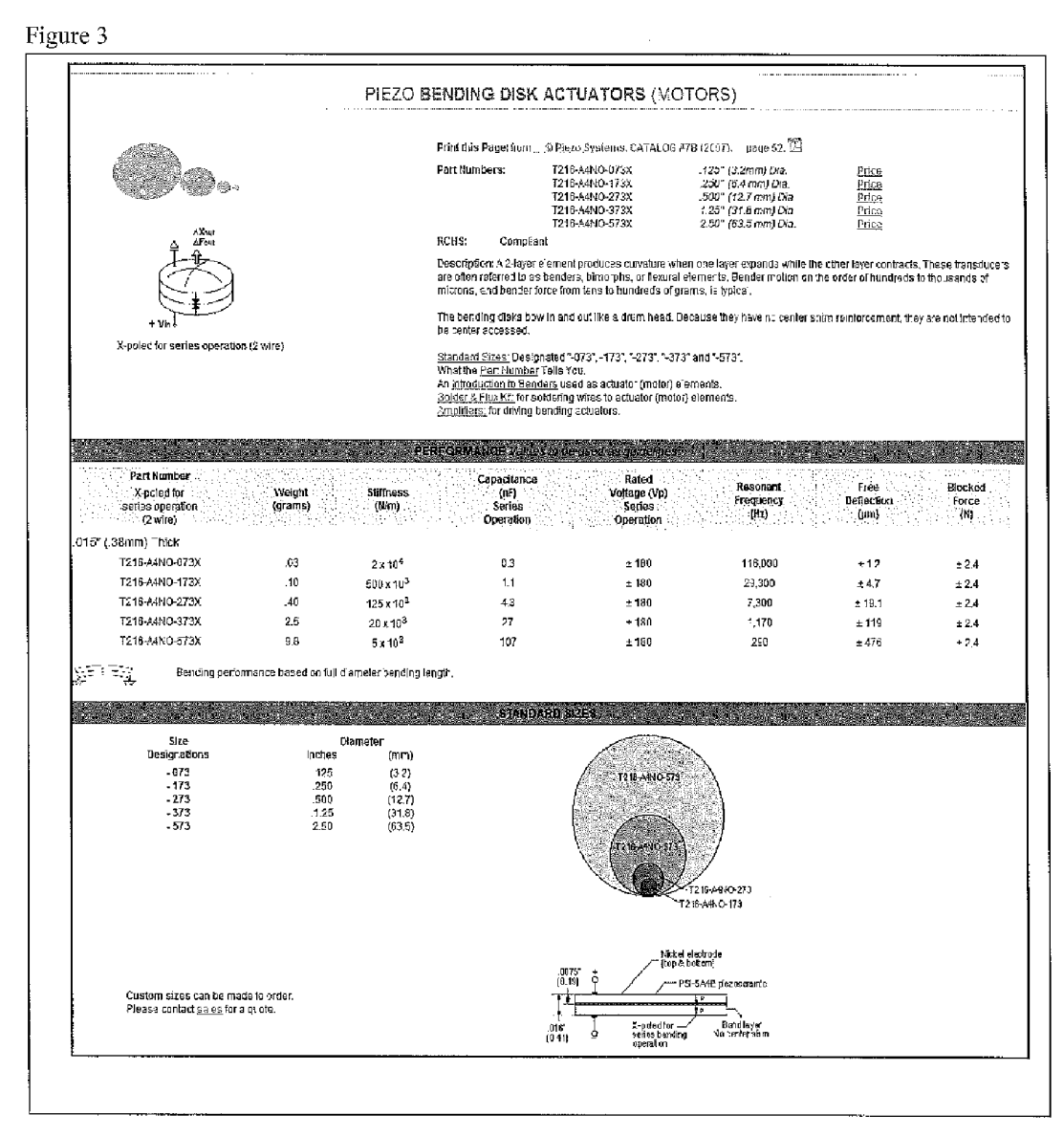

FIG. 3 shows the data sheet for different off-the-shelf piezo disks while table 1 summarizes the main characteristics of some of the disks.

TABLE 1

Performance characteristics of off-the-shelf piezo disks by Piezo Systems Inc. at the nominal working point ($F_{disk}$ = 1.2 N for all disks)

| Piezo disk designation | Diameter (mm) | $A_{disk}$ - Disk area ($m^2$) | P - Native pressure (KPa) (P = 1.2 N/A) |
|---|---|---|---|
| -073 | 3.2 | 8e-6 | 150 |
| -173 | 6.4 | 32.2e-6 | 37.2 |
| -273 | 12.7 | 126e-6 | 9.5 |
| -373 | 31.8 | 794e-6 | 1.5 |
| -573 | 63.5 | 3.1e-3 | 0.387 |

Figure 4:
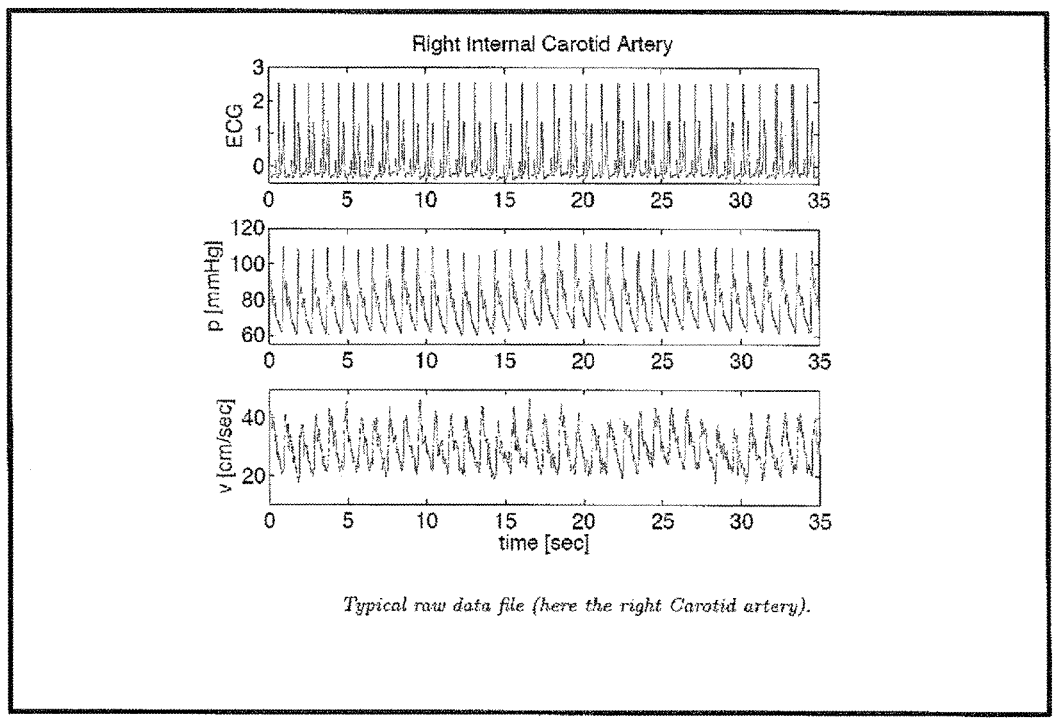
FIG. 4 shows a medical textbook chart for typical blood pressure fluctuations in one major brain artery.
Figure 5:
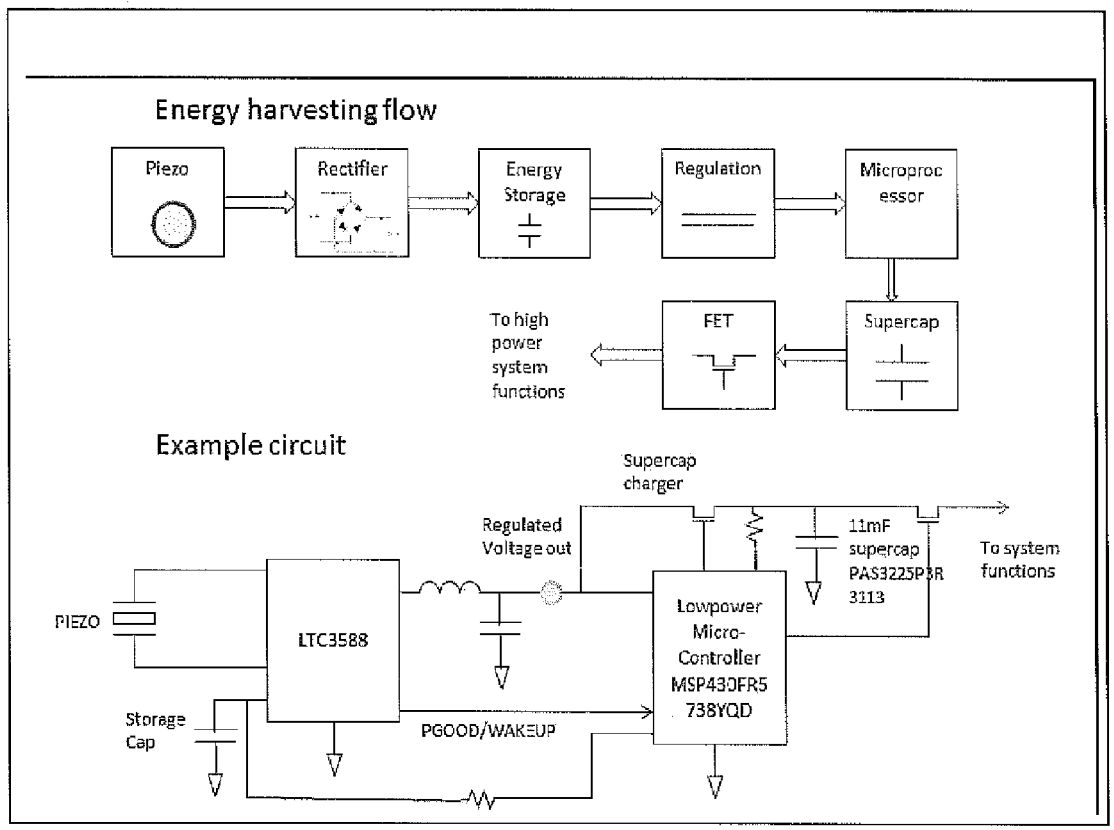
FIG. 5 in a block diagram of the power regulation and storage circuitry of the IMPG.
Figure 6:
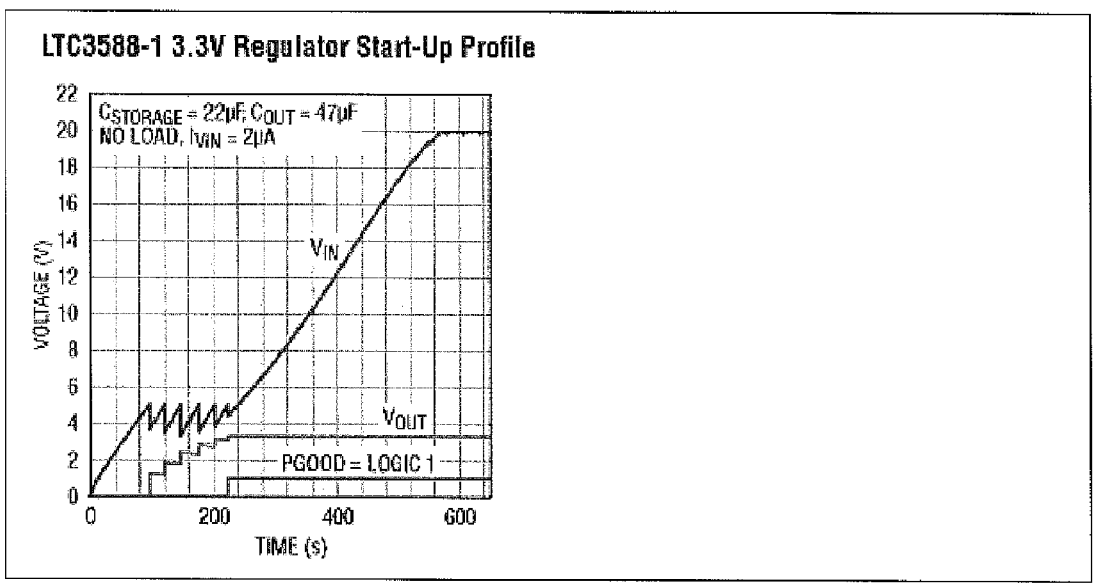
FIG. 6 presents a performance chart for a major electronic component of the regulation and storage circuit.
Figure 7:
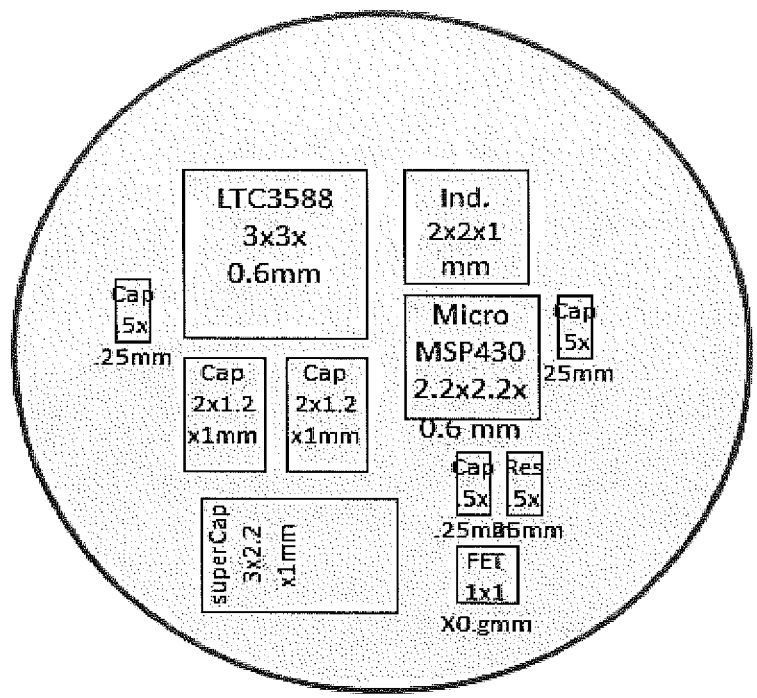
FIG. 7 illustrates one potential implementation of the regulation and storage printed circuit board's floorplan.

Another input needed for performance calculations is the blood pressure. FIG. 4 shows typical blood pressure pulses in the Right Internal Carotid Artery (Source: Blood Flow in the Circle of Willis: Modeling and Calibration—Kristen DeVault et. Al.).

From FIG. 4 the blood pressure value is between 60 mmHg and 110 mmHg with a frequency of 1 Hz. For the performance calculation the pressure variations will be taken as 25 mmHg [(110-60)/2] at a frequency of 2 Hz. The blood pressure variation in KPa is: 25 mmHg=3.3 KPa Size The purpose of the blood pressure figure is to determine whether it is strong enough to deflect the disk and create the spherical bending needed to generate power at the working point. The working point is defined as the deflection at half the blocking force of the piezo disk. In the series of disks in FIG. 3 the blocking force is 2.4N and the working point is at a pressure that can generate 1.2N on a certain disk area.

From table 1 the pressure to reach the working point is proportional to the disk area. A disk that will achieve bending to the working point at the available pressure of 3.3 KPa needs to have an area A of:

$$A = F/P = 1.2/3300 = 363 * e^{-6} \, m^2$$

This translates to a disk diameter of 21.5 mm. The IMPG diameter including the housing wall thickness is therefore 23 mm.

IMPG Size – Diameter = 23 mm

Thickness = 4 mm

Power Generation

The native voltage of the piezo disk when used as an actuator is 180V (see FIG. 3). In the IMPG application with no room for large components and with a nano-power harvesting regulator as described in section 1.1.3 below, the voltage used in the calculations will be limited to 20V. This is well below the native voltage of the piezo device and is a conservative basis for power generation assessment.

The piezo disk power generation is calculated using the following formula (obtained from Piezo Systems Inc.)

$$P_e = 2 * \pi * f * C * V^2$$

Where:
$P_e$=Electrical power
F=Frequency
C=Disk capacitance
V=operating voltage From FIG. 3 the capacitance is proportional to the disk area. The capacitance C of a 21.5 mm diameter disk is:

$$C_{21.5} = C_{12.7} * A_{21.5}/A_{12.7} = 4.3 \, nF * 363 * e^{-6} \, m^2 / 126 * e^{-6} \, m^2 = 12.4 \, nF$$

Therefore the IMPG power generation capacity in the proposed configuration is:

$$P_e = 2 * \pi * 2 * 12.4 e^{-9} * 20^2 = 62.3 \, \mu W$$

IMPG Power Generation –

$$P_e = 62.3 \, \mu W$$

$$P_e / A = 17 \, \mu W/cm^2$$

One way to address the issue of varying power requirements of implantable sensors is having a scalable solution that can generate different power levels. The IMPG concept is scalable and will produce different levels of power with different piezo disk diameters. Combined with the option described above of blood pressure coupling using a tube, different size IMPGs can be implanted in different areas in the head and power the brain sensors without having to squeeze a larger device in an area close to a brain artery.

The following is a brief description of the electrical circuitry needed for power harvesting, storage and supply, embedded in the 1 MPG.

The LTC3588 is a nano-power energy harvesting power supply. It includes rectification, storage cap switching, buck conversion, and voltage regulation into one chip. The LTC3588 is capable of storing up to 20V in the storage cap thereby maximizing the stored energy. In order to efficiently use this higher voltage, a built-in buck converter (followed by linear regulation) reduces the voltage down to 1.8V for system use. Typical start-up with 2 uA input current is shown below. Output quiescent current is less than 100 nA, and typical drain on the storage cap is less than 1000 nA.

The LTC3588 also provides a PGOOD signal, which can be used by the system as a wake-up trigger.

The MSP430FR5738 is packaged in a 2.2×2.2 mm CSP (chip scale package). It provides for uA level standby currents as contained in a 1K FRAM. The FRAM provides ultra-low power non-volatile memory storage and instant start-up. Typical current is 200 uA/MHz but ultra-low-power programming techniques can reduce average operating current <10 uA for basic required system functions. Included functions are A/D converters, SPI, UART, RTC, and 16-channel comparator.

The microprocessor provides a smart supercap charging function to charge a PAS3225P3R3113, 11 mF capacitor. External circuitry can be controlled via a FET switch, providing large, in the 10 mW range, power pulses from external circuitry. This greatly extends the operation of the otherwise low power piezo energy harvester to include low duty cycle, high power functions.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what essentially incorporates the essential idea of the invention.

I claim:

1. An implantable device for converting an in-vivo blood pressure fluctuation to electricity comprising:
    a housing comprising a sealed chamber:
    the sealed chamber comprising a wall having a piezo element disposed thereon;
    a pressure coupling tube in fluid communication with the wall and with a blood volume in a blood vessel; and;
    the wall and piezo element each configured to bend in or out from a relaxed position whereby a change in a pressure in the blood volume in the sealed chamber urges the wall and piezo element in or out from the relaxed position.

2. The device of claim 1 wherein the piezo element is a piezo-electric membrane.

3. The device of claim 1 further comprising electrical storage means.

4. The device of claim 1 further comprising power regulation circuitry.

5. The device of claim 1 further comprising communication means for electronic communication with an out-of-the-body control device.

6. The device of claim 1 further comprising wireless communication means for electronic communication with an out-of-the-body control device.

7. An implantable device for converting an in-vivo blood pressure fluctuation to electricity comprising:
    a housing comprising a sealed chamber;
    the sealed chamber comprising a wall having a piezo element disposed thereon;
    a pressure coupling tube in fluid communication with the sealed chamber;
    the pressure coupling tube and sealed chamber filled at least in part with an intermediary fluid;
    the pressure coupling tube in fluid communication with a blood volume in a blood vessel:
    a flexible membrane disposed within the pressure coupling tube separating the blood volume from the intermediary fluid whereby a fluctuation in a pressure in the blood volume is coupled through the flexible membrane and to the intermediary fluid; and;
    the wall and piezo element each configured to bend in or out from a relaxed position whereby a change in a pressure in the intermediary fluid urges the wall and piezo element in or out from the relaxed position.

8. The device of claim 7 wherein the piezo element is a piezo-electric membrane.

9. The device of claim 7 further comprising electrical storage means.

10. The device of claim 7 further comprising power regulation circuitry.

11. The device of claim 7 further comprising communication means for electronic or wireless communication with an out-of-the-body control device.

* * * * *